United States Patent
Downing

(10) Patent No.: US 8,419,670 B2
(45) Date of Patent: Apr. 16, 2013

(54) FRAME FOR AN ORTHOPEDIC BRACE HAVING A TRUSS STRUCTURE AND AN ASSOCIATED STRAPPING SYSTEM

(75) Inventor: Travis Donald Downing, Carlsbad, CA (US)

(73) Assignee: Breg, Inc., Carlsbad, CA (US)

( * ) Notice: Subject to any disclaimer, the term of this patent is extended or adjusted under 35 U.S.C. 154(b) by 226 days.

(21) Appl. No.: 13/034,588

(22) Filed: Feb. 24, 2011

(65) Prior Publication Data

US 2012/0220909 A1    Aug. 30, 2012

(51) Int. Cl.
*A61F 5/00*    (2006.01)

(52) U.S. Cl.
USPC ............... 602/26; 602/23; 602/16; 602/5

(58) Field of Classification Search ............. 602/16, 602/23, 26; D24/190–192; 128/882
See application file for complete search history.

(56) References Cited

U.S. PATENT DOCUMENTS

| | | | |
|---|---|---|---|
| 401,933 A | 4/1889 | De Camp | |
| 3,581,741 A | 6/1971 | Rosman et al. | |
| 3,669,105 A | 6/1972 | Castiglia | |
| 4,241,730 A | 12/1980 | Helfet | |
| 4,481,941 A | 11/1984 | Rolfes | |
| 4,506,661 A | 3/1985 | Foster | |
| 4,632,098 A | 12/1986 | Grundei et al. | |
| 4,805,606 A | 2/1989 | McDavid, III | |
| 4,940,044 A | 7/1990 | Castillo | |
| 5,002,045 A | 3/1991 | Spademan | |
| 5,277,698 A | 1/1994 | Taylor | |
| D346,028 S | 4/1994 | Lengyel | |
| 5,336,161 A | 8/1994 | Lengyel | |
| 5,383,845 A | 1/1995 | Nebolon | |
| 5,433,699 A | 7/1995 | Smith, III | |
| 5,512,039 A | 4/1996 | White | |
| 5,562,605 A | 10/1996 | Taylor | |
| 5,672,152 A | 9/1997 | Mason et al. | |
| 5,743,865 A | 4/1998 | Townsend | |
| 5,772,618 A | 6/1998 | Mason et al. | |
| 5,782,780 A | 7/1998 | Mason et al. | |
| 5,797,864 A | 8/1998 | Taylor | |
| 5,827,208 A | 10/1998 | Mason et al. | |
| D416,624 S * | 11/1999 | Nauert | D24/190 |
| 6,287,268 B1 | 9/2001 | Gilmour | |
| 6,623,439 B2 | 9/2003 | Nelson et al. | |

(Continued)

FOREIGN PATENT DOCUMENTS

DE    846895    8/1952

OTHER PUBLICATIONS

Partial Search Report issued by the EPO on May 25, 2012 in corresponding European Patent Application No. 12156713.5 which claims priority of the instant application.

*Primary Examiner* — Patricia Bianco
*Assistant Examiner* — Camtu Nguyen
(74) *Attorney, Agent, or Firm* — Rodney F. Brown

(57) ABSTRACT

A frame is provided for an orthopedic brace having an upper frame assembly, a lower frame assembly, a first hinge and a second hinge. The first and second hinges dynamically connect the upper and lower frame assemblies. The upper or lower frame assembly includes a truss unit which defines a triangle. The first side of the triangle is a substantially vertical longitudinal strut. The second side of the triangle is a first cross beam which is substantially horizontal or diagonal. The third side of the triangle is a diagonal second cross beam.

35 Claims, 5 Drawing Sheets

U.S. PATENT DOCUMENTS 6,740,054 B2 5/2004 Stearns
6,878,126 B2 4/2005 Nelson et al.
7,479,122 B2 1/2009 Ceriani et al.
7,534,219 B2 5/2009 Stearns \* cited by examiner

US 8,419,670 B2

FRAME FOR AN ORTHOPEDIC BRACE HAVING A TRUSS STRUCTURE AND AN ASSOCIATED STRAPPING SYSTEM

BACKGROUND OF THE INVENTION

The present invention relates generally to orthopedic braces, and more particularly to a rigid frame for an orthopedic brace which has a truss structure and an associated strapping system.

Orthopedic braces embody a broad range of structures, each having the common purpose of supporting and/or stabilizing a skeletal joint when worn on the body of a user. The orthopedic brace may serve either a preventative role or a remedial role. In a preventative role, the brace provides added support and stability to a healthy skeletal joint, thereby reducing the risk of injury when the joint is subjected to undue stress. In a remedial role, the brace supports and stabilizes a skeletal joint which has been weakened by injury or other infirmity, thereby reinforcing the joint and reducing the risk of further injury while the joint is rehabilitated.

Conventional orthopedic braces typically include a frame consisting of a plurality of rigid support members positioned adjacent to the body on either side of the affected skeletal joint being stabilized. The rigid support members are dynamically interconnected by one or more rotational hinges, which are positioned adjacent to the skeletal joint being stabilized. Thus, a conventional knee brace typically includes a frame having a rigid upper support member positioned adjacent to the upper leg and a rigid lower support member positioned adjacent to the lower leg. A rotational hinge positioned adjacent to the knee dynamically interconnects the rigid upper and lower support members. The knee brace is typically secured to the leg by a plurality of straps. An example of a prior art knee brace is disclosed in U.S. Pat. No. 7,479,122, which is incorporated herein by reference.

The present invention generally recognizes a need for an improved frame for an orthopedic brace which exhibits superior functional performance characteristics in supporting and/or stabilizing a skeletal joint of the user. Accordingly, it is an generally an object of the present invention to provide a frame for an orthopedic brace which satisfies the above-recited need. It is a particular object of the present invention to provide a frame for an orthopedic brace which exhibits enhanced structural rigidity, thereby increasing the degree of protection which the frame affords the affected skeletal joint. It is another particular object of the present invention to provide a frame for an orthopedic brace which exhibits enhanced suspension characteristics when mounted on the body of a user, thereby resisting rotational and translational migration of the frame to maintain the frame in an optimal position of effectiveness relative to the affected skeletal joint during use. These objects and others are accomplished in accordance with the invention described hereafter.

SUMMARY OF THE INVENTION

The present invention is a frame for an orthopedic brace comprising an upper frame assembly, a lower frame assembly, a first hinge and a second hinge. The first and second hinges dynamically connect the upper and lower frame assemblies. The upper or lower frame assembly includes a longitudinal member engaging the first hinge on a first side of the upper or lower frame assembly and a truss unit engaging the second hinge on a second side of the upper or lower frame assembly. The truss unit defines a triangle. The first side of the triangle is a substantially vertical longitudinal strut. The second side of the triangle is a first cross beam which is preferably substantially horizontal or diagonal. The third side of the triangle is a diagonal second cross beam. The longitudinal strut engages the second cross beam at a first intersection. The longitudinal strut engages the first cross beam at a second intersection. The second cross beam engages the first cross beam at a third intersection. The longitudinal member also preferably engages the second cross beam and the first cross beam at the third intersection.

The first and second sides of the upper or lower frame assembly each has a truss fraction. The truss fraction of the first side is the width of the third intersection divided by the distance between the third intersection and the first hinge. The truss fraction of the second side is the distance between the first and second intersections divided by the distance between the second intersection and the second hinge. In accordance with one embodiment, the truss fraction of the first side is substantially less than the truss fraction of the second side. In accordance with an alternate embodiment, the truss fraction of the first side is less than about 40% and the truss fraction of the second side is greater than about 60%. In accordance with another alternate embodiment, the truss fraction of the first side is less than about 30% and the truss fraction of the second side is greater than about 70%.

The frame preferably further comprises securing strapping connected to the upper or lower frame assembly. The securing strapping posteriorly and diagonally extends relative to the longitudinal strut from the second intersection to the third intersection and extends from the third intersection to the first intersection, thereby defining a V-shaped strap pathway. In accordance with one embodiment, the securing strapping is a single securing strap extending from the second intersection to the third intersection and from the third intersection to the first intersection. In accordance with an alternate embodiment, the securing strapping is a first securing strap and a second securing strap. The first securing strap extends from the second intersection to the third intersection and the second securing strap extends from the third intersection to the first intersection.

Another characterization of the present invention is a frame for an orthopedic brace comprising an upper frame assembly, a lower frame assembly, a first hinge and a second hinge. The first and second hinge dynamically connect the upper and lower frame assemblies. The upper frame assembly includes an upper longitudinal member engaging the first hinge on a first side of the upper frame assembly and an upper truss unit engaging the second hinge on a second side of the upper frame assembly. The upper truss unit defines a triangle. The first side of the triangle is a substantially vertical upper longitudinal strut. The second side of the triangle is an upper first cross beam. The third side of the triangle is a diagonal upper second cross beam. The upper longitudinal strut engages the upper second cross beam at an upper first intersection. The upper longitudinal strut engages the upper first cross beam at an upper second intersection. The upper second cross beam engages the upper first cross beam at an upper third intersection.

The lower frame assembly includes a lower longitudinal member engaging the first hinge on a first side of the lower frame assembly and a lower truss unit engaging the second hinge on a second side of the lower frame assembly. The lower truss unit defines a triangle. The first side of the triangle is a substantially vertical lower longitudinal strut. The second side of the triangle is a lower first cross beam. The third side of the triangle is a diagonal lower second cross beam. The lower longitudinal strut engages the lower second cross beam at a lower first intersection. The lower longitudinal strut engages the lower first cross beam at a lower second intersection. The lower second cross beam engages the lower first cross beam at a lower third intersection.

The frame preferably further comprises a middle truss unit positioned between the upper and lower trusses. The middle truss unit defines a triangle. The first side of the triangle is a substantially vertical middle longitudinal strut comprising the upper and lower longitudinal members intersecting at the first hinge. The second side of the triangle is a middle first cross beam comprising the upper second cross beam. The third side of the triangle is a middle second cross beam comprising the lower second cross beam. The second and third sides of the triangle intersect at the second hinge.

The frame preferably further comprises upper securing strapping connected to the upper frame assembly. The upper securing strapping posteriorly and diagonally extends relative to the upper longitudinal strut from the upper second intersection to the upper third intersection and extends from the upper third intersection to the upper first intersection, thereby defining a V-shaped upper strap pathway. The frame also preferably further comprises lower securing strapping connected to the lower frame assembly. The lower securing strapping posteriorly and diagonally extends relative to the lower longitudinal strut from the lower second intersection to the lower third intersection and extends from the lower third intersection to the lower first intersection, thereby defining a V-shaped lower strap pathway.

The first and second sides of the upper frame assembly each has an upper truss fraction. The upper truss fraction of the first side is the width of the upper third intersection divided by the distance between the upper third intersection and the first hinge. The upper truss fraction of the second side is the distance between the upper first and second intersections divided by the distance between the upper second intersection and the second hinge. In accordance with one embodiment, the upper truss fraction of the first side is substantially less than the upper truss fraction of the second side.

The first and second sides of the lower frame assembly each has a lower truss fraction. The lower truss fraction of the first side is the width of the lower third intersection divided by the distance between the lower third intersection and the first hinge. The lower truss fraction of the second side is the distance between the lower first and second intersections divided by the distance between the lower second intersection and the second hinge. In accordance with one embodiment, the lower truss fraction of the first side is substantially less than the lower truss fraction of the second side.

Another characterization of the present invention is frame for an orthopedic brace comprising an upper frame assembly, upper securing strapping, a lower frame assembly, lower securing strapping, a first hinge and a second hinge. The upper frame assembly has an upper longitudinal member on a first side of the frame and an upper longitudinal strut on a second side of the frame. The lower frame assembly has a lower longitudinal member on the first side of the frame and a lower longitudinal strut on the second side of the frame. The first and second hinge dynamically connect the upper and lower frame assemblies.

The upper securing strapping connects to the upper frame assembly and posteriorly and diagonally extends relative to the upper longitudinal strut from a higher point on the upper longitudinal strut to the upper longitudinal member and posteriorly and diagonally extends relative to the upper longitudinal strut from the upper longitudinal member to a lower point on the longitudinal strut, thereby defining a V-shaped upper strap pathway. The lower securing strapping connects to the lower frame assembly and posteriorly and diagonally extends relative to the lower longitudinal strut from a lower point on the lower longitudinal strut to the lower longitudinal member and posteriorly and diagonally extends relative to the lower longitudinal strut from the lower longitudinal member to a higher point on the longitudinal strut, thereby defining a V-shaped lower strap pathway.

The present invention will be further understood from the drawings and the following detailed description.

DESCRIPTION OF PREFERRED EMBODIMENTS

Figure 1:
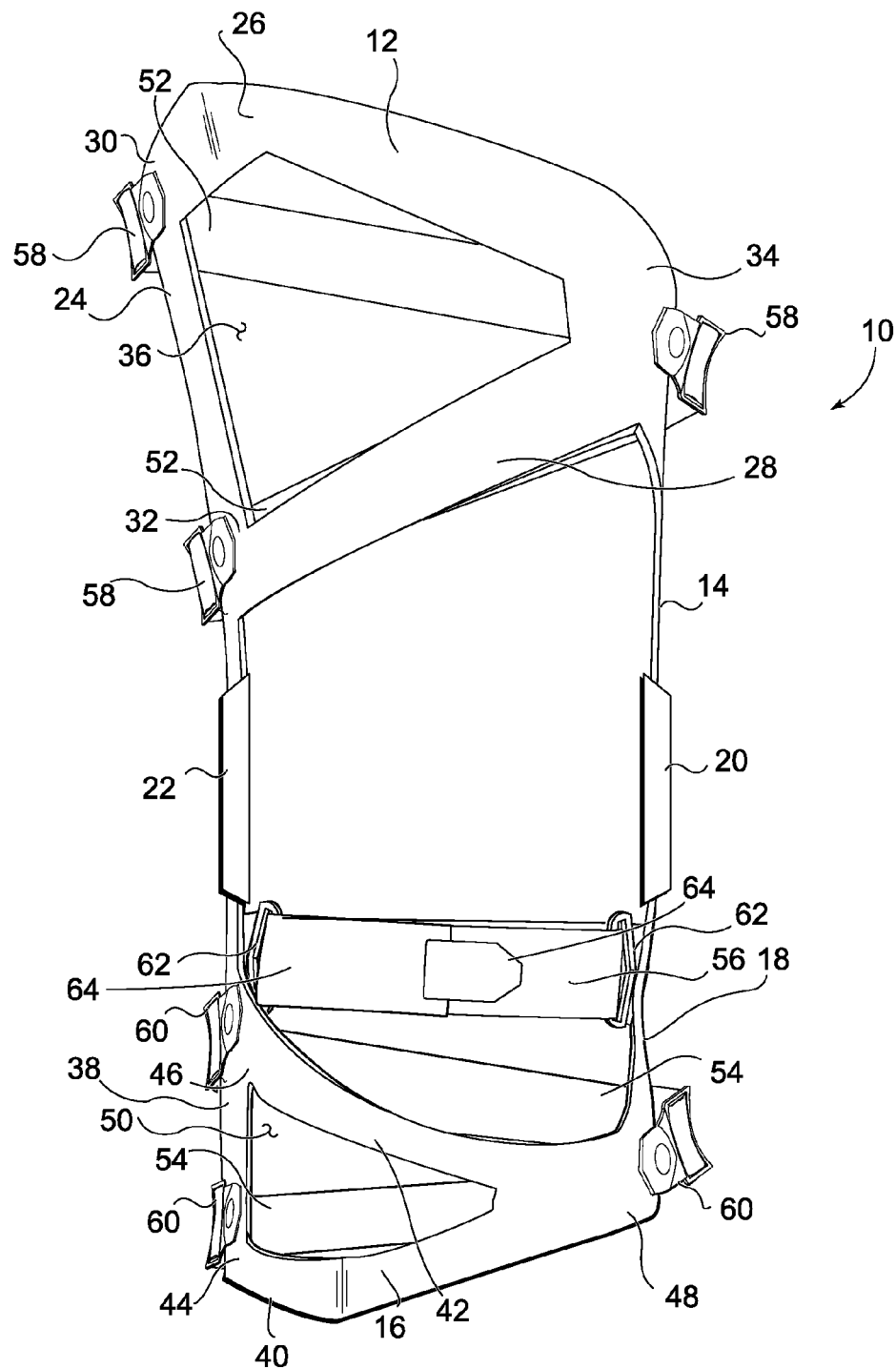
FIG. 1 is a front view of a frame for an orthopedic brace of the present invention in a position of full extension.
Figure 2:
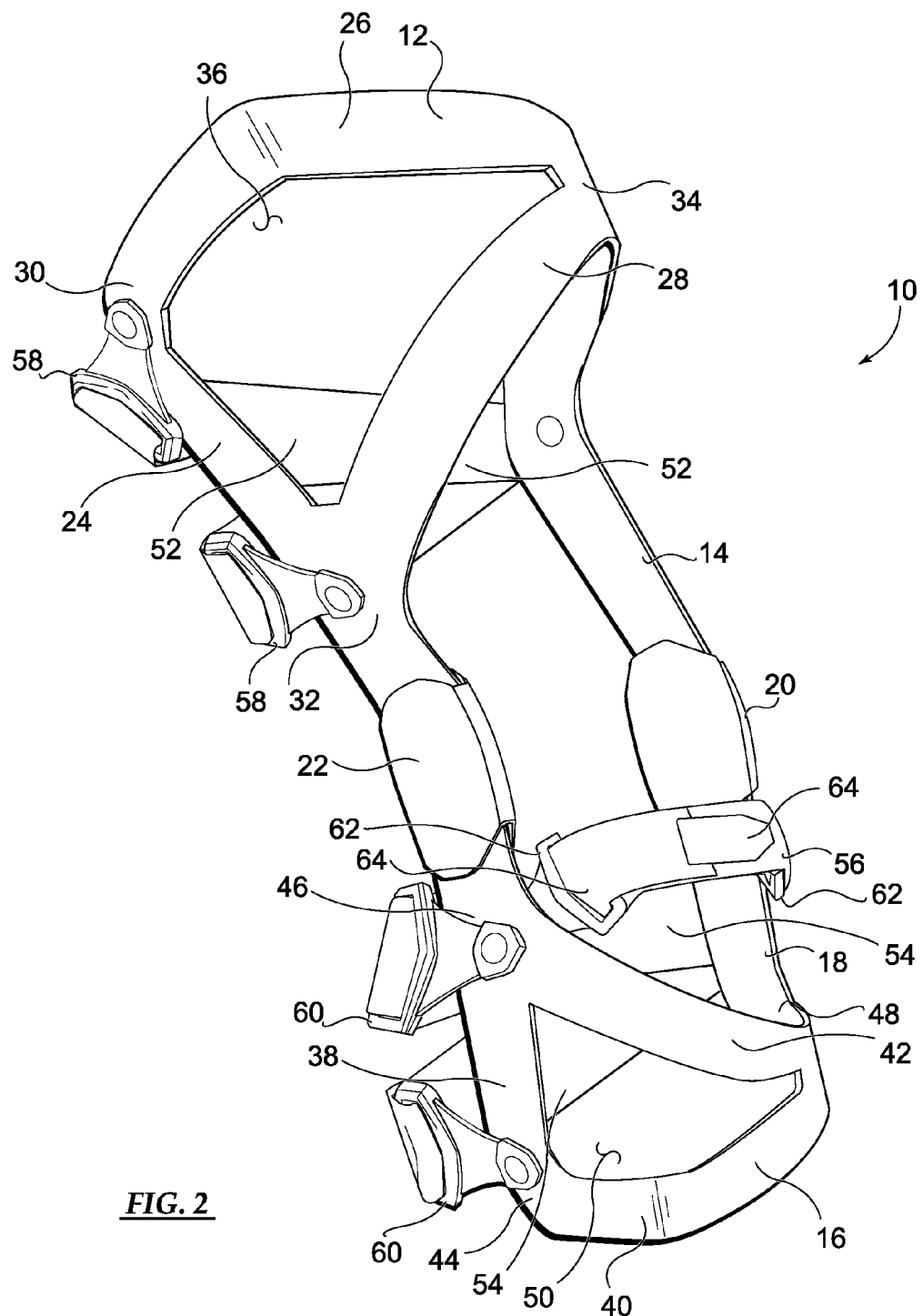
FIG. 2 is a lateral perspective view of the frame of FIG. 1 in a position of partial flexion.
Figure 3:
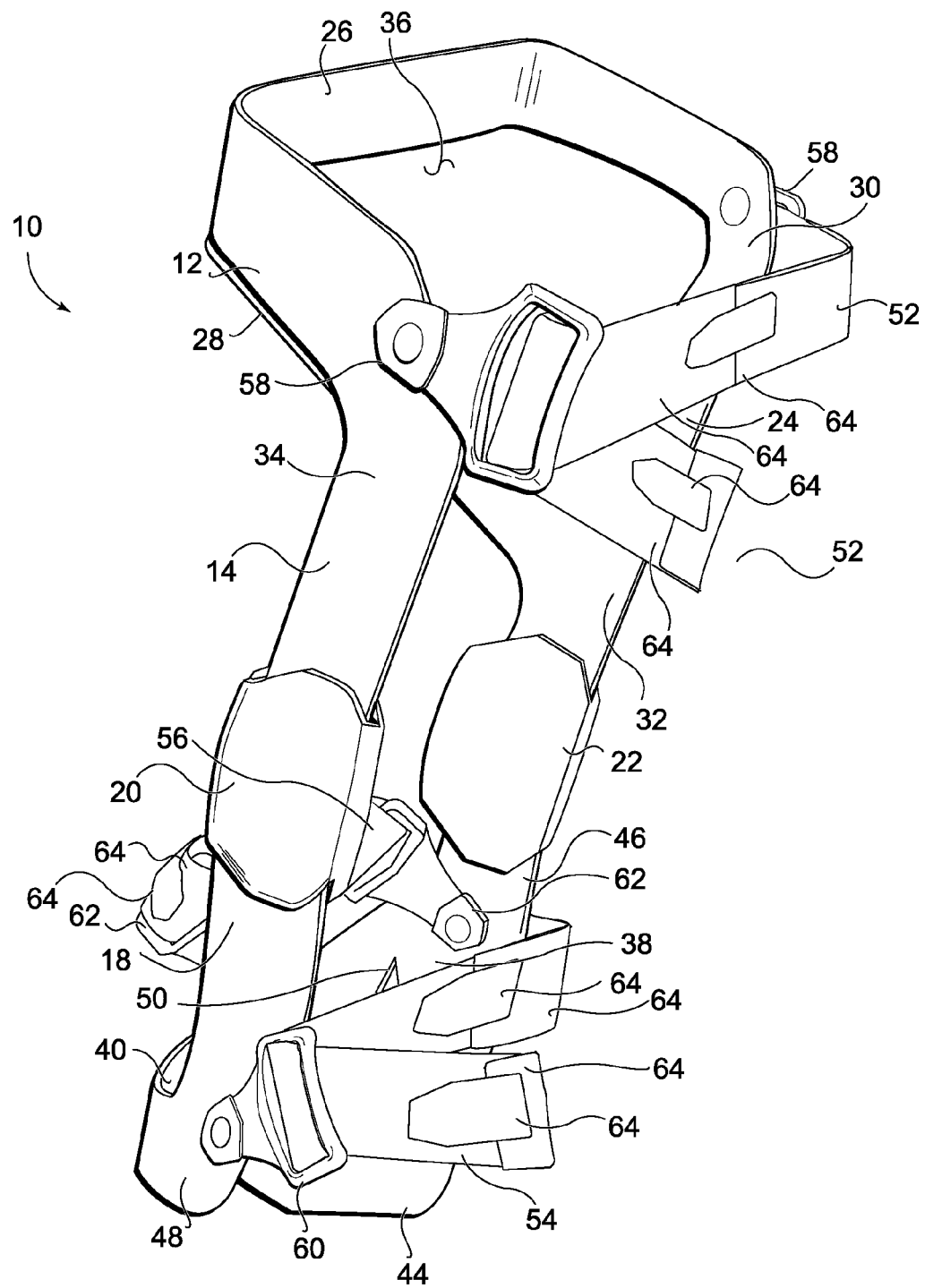
FIG. 3 is a medial perspective view of the frame of FIG. 1 in a position of partial flexion.
Figure 4:
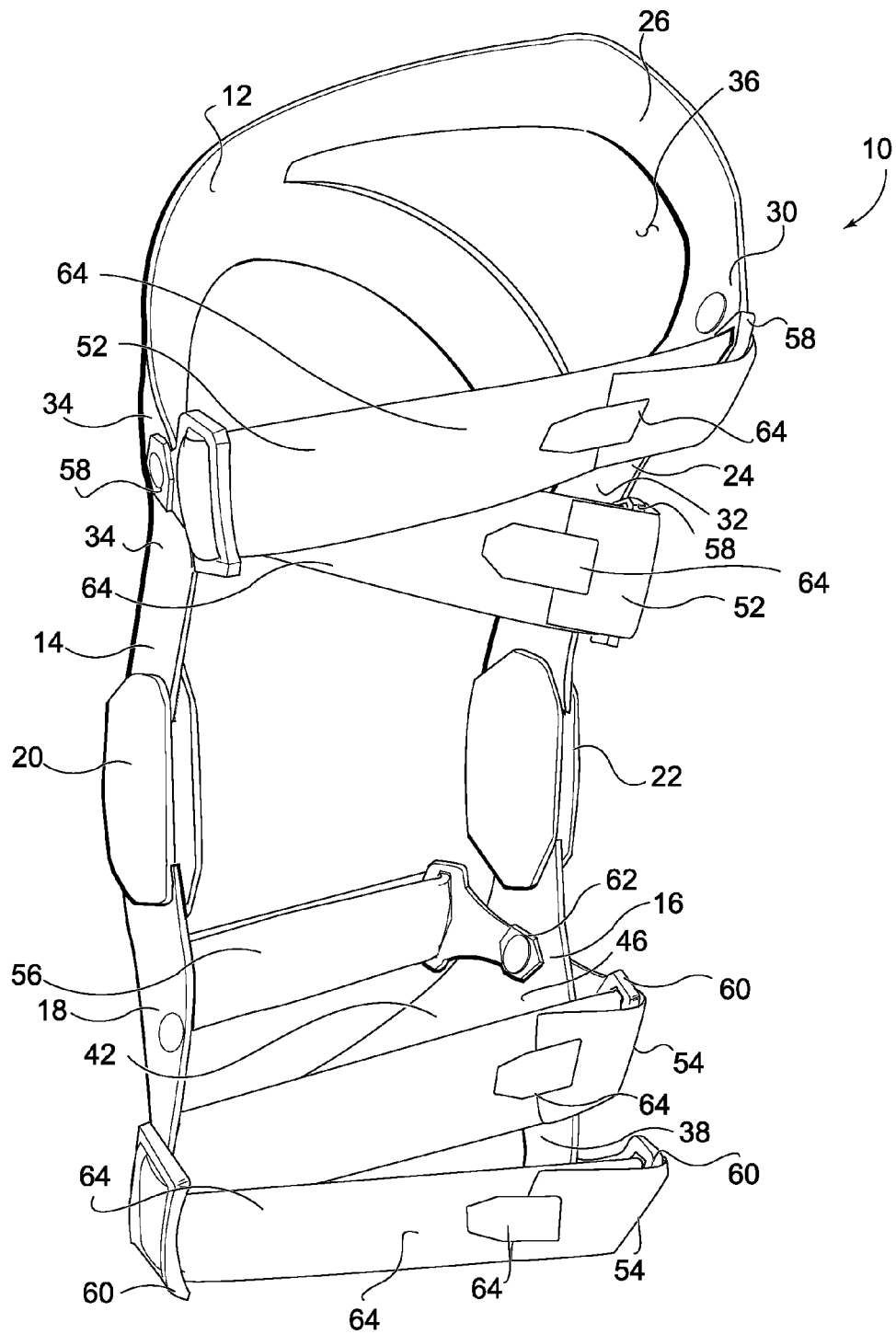
FIG. 4 is a rear perspective view of the frame of FIG. 1 in a position of partial flexion.

There are a number of relative terms defined below which are used in the following description to distinguish various elements of the frame for the orthopedic brace of the present invention from one another, but which are not to be construed as limiting the scope of the invention. The relative terms "medial" and "lateral" characterize certain elements of the frame and, in particular, describe the relative proximity of the given element to the central longitudinal axis of the body of the user when the frame is secured thereto. A "medial" element is closer to the central longitudinal axis of the body while a "lateral" element is further from the central longitudinal axis of the body.

The terms "proximal" and "distal" characterize certain elements of the frame which are aligned with the longitudinal axis of the frame. The terms describe the relative proximity of the given element to the hinges of the frame. A "proximal" element is closer to the hinges of the frame while a "distal" element is further from the hinges of the frame. The terms "upper" and "lower" likewise characterize certain elements of the frame which are aligned with the longitudinal axis of the frame. However, the terms describe the position of the given element as being either above or below a horizontal plane running through the hinges of the frame. In particular, an "upper" element is above the horizontal plane running through the hinges of the frame while a "lower" element is below the horizontal plane running through the hinges of the frame.

The relative terms "posterior" and "anterior" characterize certain elements of the frame and, in particular, describe the orientation of the given element relative to the central longitudinal axis of the body of the user when the frame is secured thereto. A "posterior" element is positioned behind the central longitudinal axis of the body in correspondence with the posterior of the body, while an "anterior" element is positioned in front of the central longitudinal axis of the body in correspondence with the anterior of the body.

Referring to FIGS. 1-4, a frame for an orthopedic brace of the present invention is shown and generally designated 10. For purposes of illustration, the frame 10 is configured as a knee brace to be worn on the right knee of a user for stabilizing the right knee. However, it is readily apparent to one of ordinary skill in the art from the teaching herein that the frame of the present invention can readily be adapted for wearing on and stabilizing the knee of the user or for wearing on and stabilizing skeletal joints of the user other than the knee.

The frame 10 comprises an upper truss unit 12, an upper longitudinal member 14, a lower truss unit 16, a lower longitudinal member 18, a first hinge 20, a second hinge 22 and an associated strapping system. Each of the upper and lower truss units 12, 16 has a triangulate construction. In particular, the upper truss unit 12 comprises a single non-planar triangle which is made up of three interconnected upper support elements, each of which constitutes a side of the triangle. The upper support elements are an upper longitudinal strut 24, an upper first cross beam 26 and an upper second cross beam 28. The upper longitudinal strut 24 is preferably substantially vertical, the upper first cross beam 26 is preferably either diagonal or substantially horizontal relative to the upper longitudinal strut 24 and the upper second cross beam 28 is preferably diagonal relative to the upper longitudinal strut 24. The intersection of the upper longitudinal strut 24 and the upper first cross beam 26 is designated 30, the intersection of the upper longitudinal strut 24 and the upper second cross beam 28 is designated 32 and the intersection of the upper first and second cross beams 26, 28 is designated 34. As is characteristic of trusses, the interior of the upper truss unit 12 is void. As such, the void space enclosed by the upper support elements 24, 26, 28 is termed an upper cutout void space 36. In accordance with preferred embodiments of the present invention, the triangular upper support elements 24, 26, 28 are preferably integrally formed with one another as a continuous unitary structure and the upper intersections 30, 34 are both preferably positioned at the uppermost edge of the frame 10 at opposing sides thereof.

The term "upper frame assembly" is used generally herein to encompass any rigid support structure of a frame which is positioned above and engages the hinges and which is displaceable about the hinges. In certain preferred embodiments set forth below, however, the term "upper frame assembly" more specifically refers to the upper truss unit 12 and upper longitudinal member 14 in combination and is designated 12, 14. In any case, the upper truss unit 12 and upper longitudinal member 14 are preferably permanently and statically affixed to one another. In particular, the upper longitudinal member 14, upper first cross beam 26 and upper second cross beam 28 are all preferably permanently and statically affixed to one another at the upper intersection 34 and are more preferably all integrally formed with one another across the upper intersection 34. As such, the upper frame assembly 12, 14 is preferably a substantially rigid unitary structure. By rigid, it is meant that the upper frame assembly 12, 14 does not substantially inelastically deform during normal use of the frame 10. However, the user can inelastically deform the upper frame assembly 12, 14, for example, by manually bending it to enhance the fit of the frame 10 on the leg of the user. Aluminum is a material exhibiting the above-described deformation characteristics and, as such, is a preferred material of construction for the upper frame assembly 12, 14. In particular, the upper frame assembly 12, 14 is preferably constructed from a unitary piece of material, e.g., a single piece of aluminum, which provides the upper frame assembly 12, 14 with a relatively high and essentially uniform degree of rigidity in its entirety.

In accordance with the embodiment shown in FIGS. 1-4, the upper truss unit 12, although non-planar, substantially approximates an obtuse scalene triangle with the upper first and second cross beams 26, 28 being diagonal relative to the substantially vertical upper longitudinal strut 24 and the upper intersections 30, 32, 34 all defining acute angles. In accordance with an alternate embodiment, not shown, the upper truss unit 12 more closely approximates a right triangle with the upper first cross beam 26 being substantially horizontal and the upper second cross beam 28 being diagonal relative to the substantially vertical upper longitudinal strut 24. As such, the diagonal upper second cross beam 28 forms the hypotenuse of the right triangle, the upper intersection 30 defines an approximately right angle of the triangle and the upper intersections 32, 34 define acute angles of the triangle. In accordance with other alternate embodiments not shown, the upper truss unit 12 substantially approximates an equilateral triangle or a non-right isosceles triangle with the upper first and second cross beams 26, 28 both being diagonal relative to the upper longitudinal strut 24 and at least two of the upper intersections 30, 32, 34 defining acute angles.

The lower truss unit 16 has a triangulate construction similar to the upper truss unit 12. As such, the lower truss unit 16 comprises a single non-planar triangle which is made up of three interconnected triangular lower support elements corresponding to like elements of the upper truss unit 12. The lower support elements are a lower longitudinal strut 38, a lower first cross beam 40 and a lower second cross beam 42 and each of the lower support elements constitutes a side of the triangle of the lower truss unit 16. The lower longitudinal strut 38 is preferably substantially vertical, the lower first cross beam 40 is preferably either diagonal or substantially horizontal relative to the lower longitudinal strut 38 and the lower second cross beam 42 is preferably diagonal relative to the lower longitudinal strut 38. The intersection of the lower longitudinal strut 38 and the lower first cross beam 40 is designated 44, the intersection of the lower longitudinal strut 38 and the lower second cross beam 42 is designated 46 and the intersection of the lower first and second cross beams 40, 42 is designated 48. As is characteristic of trusses, the interior of the lower truss unit 16 is void. As such, the void space enclosed by the lower support elements 38, 40, 42 is termed a lower cutout void space 50. In accordance with preferred embodiments of the present invention, the triangular lower support elements 38, 40, 42 are preferably integrally formed with one another as a continuous unitary structure and the lower intersections 44, 48 are both preferably positioned at the lowermost edge of the frame 10 at opposing sides thereof.

The term "lower frame assembly" is used generally herein to encompass any rigid support structure of a frame which is positioned below and engages the hinges and which is displaceable about the hinges. In certain preferred embodiments set forth below, however, the term "lower frame assembly" more specifically refers to the lower truss unit 16 and lower longitudinal member 18 in combination and is designated 16, 18. In any case, the lower truss unit 16 and lower longitudinal member 18 are, like the upper truss unit 12 and upper longitudinal member 14, preferably permanently and statically affixed to one another. In particular, the lower longitudinal member 18, lower first cross beam 40 and lower second cross beam 42 are all preferably permanently and statically affixed to one another at the lower intersection 48 and are more preferably all integrally formed with one another across the lower intersection 48. As such, the lower frame assembly 16, 18 is preferably a substantially rigid unitary structure. The lower frame assembly 16, 18 is preferably constructed from the same or similar materials as the upper frame assembly 12, 14 in substantially the same or similar manner and, as such, preferably exhibits substantially the same deformation characteristics.

Figure 5:
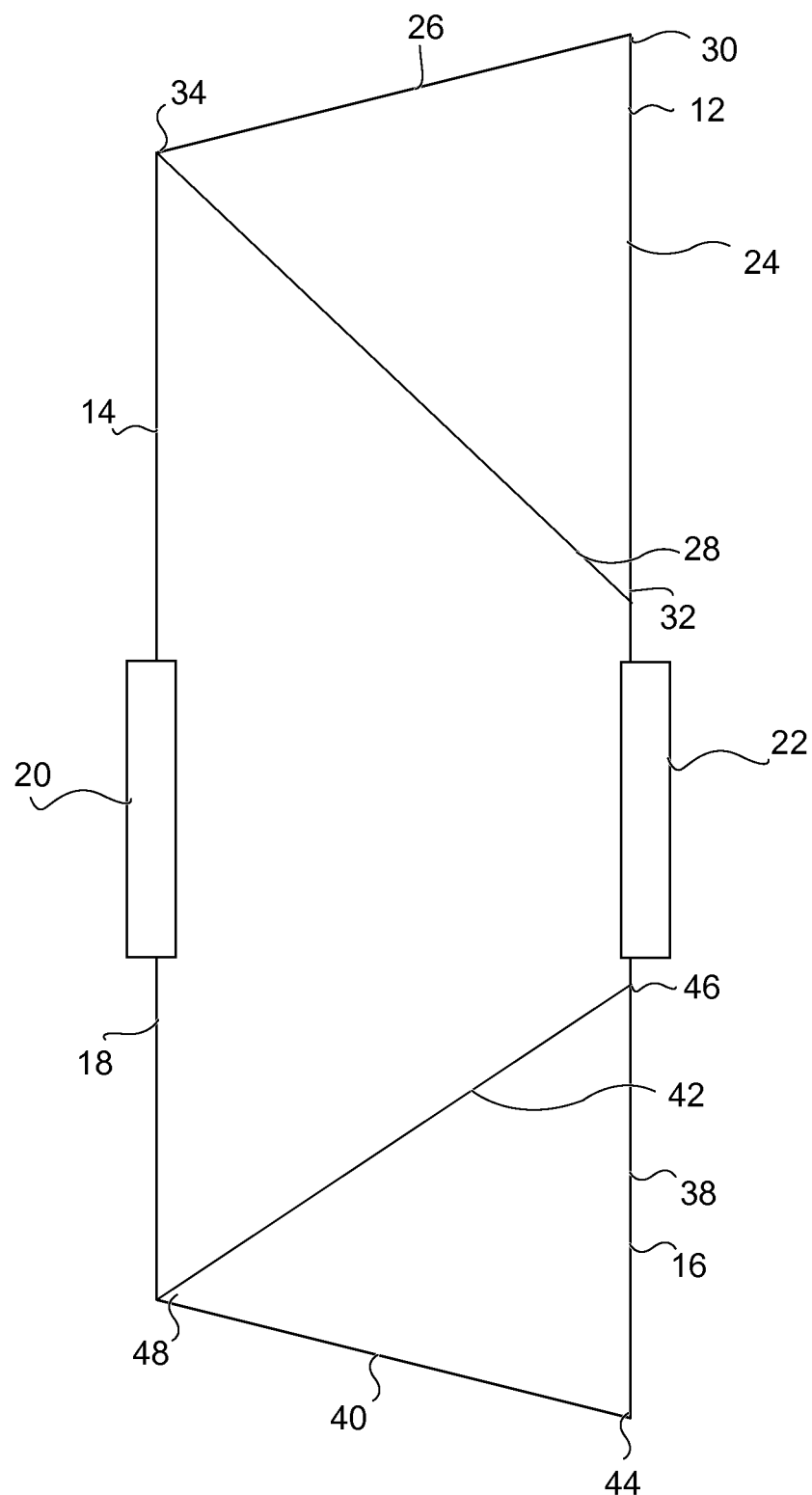
FIG. 5 is a conceptualized two-dimensional frontal representation of the frame of the present invention in a position of full extension.

In accordance with the embodiment shown in FIGS. 1-4, the lower truss unit 16, although non-planar, substantially approximates an obtuse scalene triangle with the lower first and second cross beams 40, 42 being diagonal relative to the substantially vertical lower longitudinal strut 38 and the lower intersections 44, 46, 48 all defining acute angles. In accordance with an alternate embodiment, not shown, the lower truss unit 16 more closely approximates a right triangle with the lower first cross beam 40 being substantially horizontal and the lower second cross beam 42 being diagonal relative to the substantially vertical lower longitudinal strut 38. As such, the diagonal lower second cross beam 42 forms the hypotenuse of the right triangle, the lower intersection 44 defines an approximately right angle of the triangle and the lower intersections 46, 48 define acute angles of the triangle. In accordance with other alternate embodiments not shown, the lower truss unit 16 substantially approximates an equilateral triangle or a non-right isosceles triangle with the lower first and second cross beams 40, 42 both being diagonal relative to the lower longitudinal strut 38 and at least two of the lower intersections 44, 46, 48 defining acute angles. FIG. 5 is a conceptualized two-dimensional representation of the frame 10 showing the triangulate construction of the upper and lower truss units 12, 16.

The upper and lower frame assemblies 12, 14 and 16, 18 are dynamically connected to one another across the first and second hinges 20, 22. In particular, the first hinge 20 dynamically connects the upper and lower longitudinal members 14, 18 on one side of the frame 10 and the second hinge 22 dynamically connects the upper and lower truss units 12, 16 on the opposing side of the frame 10. The upper longitudinal member 14 is an elongate segment extending essentially the entire length of one side of the upper frame assembly 12, 14. The upper longitudinal member 14 extends downwardly from the upper intersection 34 into top of the first hinge 20 to engage the first hinge 20. The lower longitudinal member 18 is similarly configured as an elongate segment extending the length of the corresponding side of the lower frame assembly 16, 18. The lower longitudinal member 18 extends upwardly from the lower intersection 48 into the bottom of the first hinge 20 to engage the first hinge 20.

The first hinge 20 is preferably a rotational hinge which rotationally connects the upper and lower longitudinal members 14, 18 on one side of the frame 10 and enables rotational displacement of the upper and lower longitudinal members 14, 18 about the first hinge 20 between positions of extension and flexion. The axis of rotation of the first hinge 20 is essentially perpendicular to the orientation of the upper and lower longitudinal members 14, 18. Details of the structure and operation of a representative rotational hinge having utility as the first hinge 20 of the frame 10 are disclosed in U.S. Pat. No. 5,772,618, which is incorporated herein by reference. However, it is understood that the first hinge 20 is not limited to any one specific construction or type of rotational hinge. Thus, most conventional rotational hinges for orthopedic braces, which enable rotation of two rigid members about the hinge, can alternately be employed as the first hinge 20 of the frame 10. Exemplary additional prior art hinges are disclosed in U.S. Pat. Nos. 401,933; 4,481,941; 5,672,152; and 5,827,208. In accordance with a preferred embodiment, the first hinge 20 is essentially rigid (i.e., inflexible) in the mediolateral direction.

The second hinge 22 dynamically connects the upper and lower truss units 12, 16 to one another on the opposing side of the frame 10 from the first hinge 20 by means of the upper and lower longitudinal struts 24, 38. Although the upper and lower longitudinal struts 24, 38 constitute sides of the upper and lower truss units 12, 16, respectively, whereas the upper and lower longitudinal members 14, 18 do not constitute part of either the upper or lower truss unit 12, 16, the upper and lower longitudinal struts 24, 38 are, nevertheless, similarly configured to the upper and lower longitudinal members 14, 18. In particular, the upper longitudinal strut 24 is an elongate segment extending essentially the entire length of the side of the upper frame assembly 12, 14 opposite the upper longitudinal member 14. The upper longitudinal strut 24 extends downwardly from the upper intersection 30 to the upper intersection 32 and into the top of the second hinge 22 to engage the second hinge 22. Although the upper longitudinal strut 24 extends a relatively short length beyond the upper intersection 32 into the top of the second hinge 22, this extension length is short relative to the overall length of the upper frame assembly 12, 14 so that the upper intersection 32 is deemed effectively adjacent to the second hinge 22.

The lower longitudinal strut 38 is an elongate segment extending the length of the opposite side of the lower frame assembly 16, 18 corresponding to the upper longitudinal strut 24. The lower longitudinal strut 38 extends upwardly from the lower intersection 44 to the lower intersection 46 and into the bottom of the second hinge 22 to engage the second hinge 22. Although the lower longitudinal strut 38 extends a relatively short length beyond the lower intersection 46 into the bottom of the second hinge 22, this extension length is short relative to the overall length of the lower frame assembly 16, 18 so that the lower intersection 46 is deemed effectively adjacent to the second hinge 22. It is noteworthy that although the upper and lower truss units 12, 16 effectively intersect at the second hinge 22, the upper and lower truss units 12, 16 do not share any common sides with one another. As such, each upper and lower truss unit 12, 16 constitutes its own independent single-triangle truss relative to the other truss.

The second hinge 22 is preferably a rotational hinge which rotationally connects the upper and lower longitudinal struts 24, 38 and which is structurally and functionally the same or similar to the first hinge 20. The second hinge 22 enables rotational displacement of the upper and lower longitudinal struts 24, 38 about the second hinge 22 between positions of extension and flexion. The axis of rotation of the second hinge 22 is essentially perpendicular to the orientation of the upper and lower longitudinal struts 24, 38.

The elements of the frame 10 described herein are not limited to any particular dimensions, but are sized commensurate with the size of a typical user. Nevertheless, it is instructive to recite exemplary dimensions herein of certain frame elements to provide teaching of preferred dimensional relationships between the various frame elements. As such, the side of the upper frame assembly 12, 14 which includes the upper longitudinal member 14 may have an exemplary length on the order of about 5 inches from the upper intersection 34 to the first hinge 20. The corresponding side of the lower frame assembly 16, 18 which includes the lower longitudinal member 18 may have an exemplary length on the order of about 4 inches from the lower intersection 48 to the first hinge 20. The opposite side of the upper frame assembly 12, 14 which includes the upper longitudinal strut 24 may have an exemplary length on the order of about 6 inches from the upper intersection 30 to the second hinge 22, thereby approximating, but slightly more than, the length of the other upper side. The corresponding side of the lower frame assembly 16, 18 which includes the lower longitudinal strut 38 may have an exemplary length on the order of about 5 inches from the lower intersection 44 to the second hinge 22, thereby approximating, but slightly more than, the length of the other lower side.

An exemplary extension length of the upper and lower longitudinal struts 24, 38 may be on the order of about 1 inch from the upper and lower intersections 32, 46, respectively, to the second hinge 22. An exemplary length of the upper intersection 34, which is defined herein as the width of the upper first cross beam 26 at the upper intersection 34, is on the order of about 1.5 inches. An exemplary length of the lower intersection 48, which is defined herein as the width of the lower first cross beam 40 at the lower intersection 48, is on the order of about 1 inch.

The length of the upper truss unit 12 on the side of the upper frame assembly 12, 14 on which the second hinge 22 resides is defined as the distance between the upper intersections 30, 32 while the entire length of this side of the upper frame assembly 12, 14 is defined as the distance between the upper intersection 30 and the second hinge 22. In accordance with the present invention, the length of the upper truss 12 is preferably a relatively substantial fraction of the entire side. In the above-recited dimensional example of the frame 10, this fraction, termed the upper truss fraction, is on the order of greater than about 80%. In contrast, the length of the upper truss unit 12 on the opposite side of the upper frame assembly 12, 14 on which the first hinge 20 resides, i.e., the length of the upper intersection 34, is preferably a relatively smaller fraction of the entire length of this side of the upper frame assembly 12, 14. In the above-recited dimensional example of the frame 10, this upper truss fraction is on the order of less than about 30%.

Similarly, the length of the lower truss unit 16 on the side of the lower frame assembly 16, 18 on which the second hinge 22 resides is defined as the distance between the lower intersections 44, 46 while the entire length of this side of the lower frame assembly 16, 18 is defined as the distance between the lower intersection 44 and the second hinge 22. In accordance with the present invention, the length of the lower truss 16 is preferably a relatively substantial fraction of the entire side. In the above-recited dimensional example of the frame 10, this fraction, termed the lower truss fraction, is also on the order of greater than about 80%. In contrast, the length of the lower truss unit 16 on the opposite side of the lower frame assembly 16, 18 on which the first hinge 20 resides, i.e., the length of the lower intersection 48, is preferably a relatively smaller fraction of the entire length of this side of the lower frame assembly 16, 18. In the above-recited dimensional example of the frame 10, this lower truss fraction is likewise on the order of less than about 30%.

In sum, it is preferable that each of the upper and lower frame assemblies 12, 14 and 16, 18 exhibit a truss fraction greater than 50% on one side of the corresponding upper or lower frame assembly 12, 14 or 16, 18 and a truss fraction less than 50% on the opposite side of the corresponding upper or lower frame assembly 12, 14 or 16, 18. It is more preferable that each of the frame assemblies 12, 14 and 16, 18 exhibit a truss fraction greater than 60% on one side of the corresponding frame assembly and a truss fraction less than 40% on the opposite side of the corresponding frame assembly. It is more preferable that each of the frame assemblies 12, 14 and 16, 18 exhibit a truss fraction greater than 70% on one side of the corresponding frame assembly and a truss fraction less than 30% on the opposite side of the corresponding frame assembly. A frame assembly having the above-recited preferred truss fractions enhances the effectiveness of the frame 10 as a joint support compared to alternately configured prior art structures because a frame having a truss structure as disclosed herein has more strength and rigidity than a frame of the equivalent weight having an alternate configuration.

When the frame 10 is mounted on a leg of a user, the first and second hinges 20, 22 engage the opposing sides of the knee of the user and the upper truss unit 12 extends across and engages the anterior thigh of the user above the knee. The arcuate interior face of the upper truss unit 12 is in essential conformance with the arcuate contour of the anterior thigh, thereby functioning as a thigh cuff. The lower truss unit 16 correspondingly extends across and engages the shin of the user below the knee. The arcuate interior face of the lower truss unit 16 is in essential conformance with the arcuate contour of the shin, thereby functioning as a shin cuff. Additionally when mounting the frame 10 on the leg (the right leg in this case), the side of the upper and lower frame assemblies 12, 14 and 16, 18 having the greater truss fraction is preferably positioned on the lateral side of the leg while the opposite side of the upper and lower frame assemblies 12, 14 and 16, 18 having the lesser truss fraction is preferably positioned on the medial side of the leg. As a general rule, the lateral side of the leg is typically more vulnerable to external impact forces, thereby creating a need for greater rigidity and support from a brace frame on that side of the leg.

It is further apparent from the above-recited dimensional example that the side of the frame 10 preferably positioned on the medial side of leg also preferably has a total length which is somewhat less than the total length of the opposite side of the frame 10 preferably positioned on the lateral side of the leg. A shorter medial side of the frame 10 enhances the bilateral clearance of the frame 10 with respect to the unaffected leg and, thus, enhances the comfort of the user. As a result, the frame 10 more readily accommodates active sports such as skiing, snowboarding, dirt bike riding, horseback riding and the like which require close engagement of the affected leg.

The frame 10 further includes an associated strapping system which comprises a plurality of securing straps, namely, an upper posterior strap 52, a lower posterior strap 54 and a lower anterior strap 56. The strapping system further comprises a plurality of strap retainers, namely upper posterior strap retainers 58, lower posterior strap retainers 60 and lower anterior strap retainers 62. The securing straps 52, 54, 56 are each flexible, yet relatively non-stretchable, cloth straps which closely secure the frame 10 to the leg of a user. Each securing strap 52, 54, 56 is preferably provided with releasable fasteners 64. An embodiment of the fastener 64 is the hook or loop material of a hook-and-loop fastener commonly known by the trade name VELCRO. In this embodiment, a patch of hook material is permanently attached to both ends of each securing strap 52, 54, 56 by sewing or the like while the outside face of the body of the securing strap 52, 54, 56 is preferably continuously covered with, or integrally formed from, loop material. This enables a user to adjust the length of the securing straps 52, 54, 56 to any desired length in a manner described below.

The upper posterior strap 52 is a partial circumferential strap which extends posteriorly around the posterior thigh above the knee in a semicircular back and forth path between the upper longitudinal member 14 and the upper longitudinal strut 24 of the upper frame assembly 12, 14. The upper posterior strap retainers 58 are attached to the upper frame assembly 12, 14 and enable adjustable connection of the upper posterior strap 52 to the frame 10. In particular, an upper posterior strap retainer 58 is permanently, but rotatably, attached by a rivet to the upper frame assembly 12, 14 at the upper intersection 30, an upper posterior strap retainer 58 is permanently, but rotatably, attached by a rivet to the upper frame assembly 12, 14 at the upper intersection 32 and an upper posterior strap retainer 58 is permanently, but rotatably, attached by a rivet to the upper frame assembly 12, 14 at the upper intersection 34. The upper posterior strap retainers 58 at the upper intersections 30, 32, 34 slidably receive the upper posterior strap 52 enabling adjustable connection of the upper posterior strap 52 to the upper frame assembly 12, 14 in a manner described below.

The lower posterior strap 54 is a partial circumferential strap which extends posteriorly around the calf below the knee in a semicircular back and forth path between the lower longitudinal member 18 and the lower longitudinal strut 38 of the lower frame assembly 16, 18. The lower posterior strap retainers 60 are attached to the lower frame assembly 16, 18 and enable adjustable connection of the lower posterior strap 54 to the frame 10. In particular, a lower posterior strap retainer 60 is permanently, but rotatably, attached by a rivet to the lower frame assembly 16, 18 at the lower intersection 44, a lower posterior strap retainer 60 is permanently, but rotatably, attached by a rivet to the lower frame assembly 16, 18 at the lower intersection 46 and a lower posterior strap retainer 60 is permanently, but rotatably, attached by a rivet to the lower frame assembly 16, 18 at the lower intersection 48. The lower posterior strap retainers 60 at the lower intersections 44, 46, 48 slidably receive the lower posterior strap 54 enabling adjustable connection of the lower posterior strap 54 to the lower frame assembly 16, 18 in a manner described below.

The lower anterior strap 56 is a partial circumferential strap which extends anteriorly around the shin below the knee, but above the lower first cross beam 40, in a semicircular path between the lower longitudinal member 18 and the lower longitudinal strut 38 of the lower frame assembly 16, 18. The lower anterior strap retainers 62 are attached to the lower frame assembly 16, 18 and enable adjustable connection of the lower anterior strap 56 to the frame 10. In particular, a lower anterior strap retainer 62 is permanently, but rotatably, attached by a rivet to the lower frame assembly 16, 18 at the lower intersection 46 and a lower anterior strap retainer 62 is permanently, but rotatably, attached by a rivet to the lower frame assembly 16, 18 at the approximate mid-point of the lower longitudinal member 18. The lower anterior strap retainers 62 at the lower intersection 46 and lower longitudinal member 18 slidably receive the lower anterior strap 56 enabling adjustable connection of the lower anterior strap 56 to the lower frame assembly 16, 18 in a manner described below.

The frame 10 is snugly fitted to the leg of a user by removing the upper and lower posterior straps 52, 54 and mounting the frame 10 on the leg through the open posterior of the frame 10. One free end of the upper posterior strap 52 is threaded through a loop on the upper posterior strap retainer 58 at the upper intersection 30, doubled back over the outside face of the body of the upper posterior strap 52 and releasably fastened thereto. The remaining free end of the upper posterior strap 52 is drawn across the open upper posterior of the frame 10 and underlying posterior thigh to the upper posterior strap retainer 58 at the upper intersection 34 which is preferably positioned lower on the frame 10 than the upper posterior strap retainer 58 at the upper intersection 30. The free end is threaded through a loop on the upper posterior strap retainer 58 at the upper intersection 34 and doubled back over itself to the upper posterior strap retainer 58 at the upper intersection 32. The free end is threaded through a loop on the upper posterior strap retainer 58 at the upper intersection 32, doubled back over the outside face of the body of the upper posterior strap 52 and releasably fastened thereto, thereby completing adjustable connection of the upper posterior strap 52 to the upper frame assembly 12, 14. The upper posterior strap 52 defines a V-shaped strap pathway. As such, the upper longitudinal strut 24 and upper posterior strap 52 in combination define a triangle with the upper longitudinal strut 24 forming a substantially vertical side of the triangle and the upper posterior strap 52 forming the remaining two sides of the triangle, one of which is either diagonal or substantially horizontal and the other of which is diagonal.

The lower posterior strap 54 is similarly adjustably connected to the frame 10 by threading one free end of the lower posterior strap 54 through a loop on the lower posterior strap retainer 60 at the lower intersection 44, doubling the end back over the outside face of the body of the lower posterior strap 54 and releasably fastening the end thereto. The remaining free end of the lower posterior strap 54 is drawn across the open lower posterior of the frame 10 and underlying calf to the lower posterior strap retainer 60 at the lower intersection 48 which is preferably positioned higher on the frame 10 than the lower posterior strap retainer 60 at the lower intersection 44. The free end is threaded through a loop on the lower posterior strap retainer 60 at the lower intersection 48 and doubled back over itself to the lower posterior strap retainer 60 at the lower intersection 46. The free end is threaded through a loop on the lower posterior strap retainer 60 at the lower intersection 46, doubled back over the outside face of the body of the lower posterior strap 54 and releasably fastened thereto, thereby completing adjustable connection of the lower posterior strap 54 to the lower frame assembly 16, 18. The lower posterior strap 54 defines a V-shaped strap pathway. As such, the lower longitudinal strut 38 and lower posterior strap 54 in combination define a triangle with the lower longitudinal strut 38 forming the remaining two sides of the triangle, one of which is either diagonal or substantially horizontal and the other of which is diagonal.

The lower anterior strap 56 is adjustably connected to the frame 10 by threading one free end of the lower anterior strap 56 through a loop on the lower anterior strap retainer 62 at the lower intersection 46, doubling the end back over the outside face of the body of the lower anterior strap 56 and releasably fastened the end thereto. The remaining free end of the lower anterior strap 56 is drawn across the open lower anterior of the frame 10 and underlying shin to the lower anterior strap retainer 62 at the mid-point of the lower longitudinal member 18. The free end is threaded through a loop on the lower anterior strap retainer 62 at the mid-point of the lower longitudinal member 18, doubled back over the outside face of the body of the lower anterior strap 56 and releasably fastened thereto, thereby completing adjustable connection of the lower anterior strap 56 to the lower frame assembly 16, 18.

The user is able to adjust the strap length and strap tension by selection of the point on the strap body where the strap end is releasably fastened. In particular, each of the securing straps 52, 54, 56 may be tightened or loosened by shortening or lengthening the securing straps 52, 54, 56, thereby enabling the user to adjust the fit of the frame 10 to the leg and correspondingly to adjust the degree of support and stability the frame 10 provides the knee. Lengthening the upper posterior strap 52, thereby loosening the upper posterior strap 52, is effected by releasably fastening one end of the upper posterior strap 52 to a point on the body of the upper posterior strap 52 closer to the upper posterior strap retainer 58 at the upper intersection 30 and/or by releasably fastening the other end of the upper posterior strap 52 to a point on the body of the upper posterior strap 52 closer to the upper posterior strap retainer 58 at the upper intersection 32. Shortening the upper posterior strap 52, thereby tightening the upper posterior strap 52, is effected by releasably fastening one end of the upper posterior strap 52 to a point on the body of the upper posterior strap 52 farther from the upper posterior strap retainer 58 at the upper intersection 30 and/or by releasably fastening the other end of the upper posterior strap 52 to a point on the body of the upper posterior strap 52 farther from the upper posterior strap retainer 58 at the upper intersection 32. Lengthening and shortening the lower posterior strap 54 is effected in substantially the same manner as above, but with respect to the lower posterior strap retainers 60 at the lower intersections 44, 46. Lengthening and shortening the lower anterior strap 56 is likewise effected in substantially the same manner as above, but with respect to the lower anterior strap retainers 62.

Although not shown, it is alternately within the scope of the present invention to substitute two upper posterior straps for the single upper posterior strap 52. In accordance with this alternative, a first upper posterior strap extends between the upper posterior strap retainer 58 at the upper intersection 30 and the upper posterior strap retainer 58 at the upper intersection 34. A second upper posterior strap extends between the upper posterior strap retainer 58 at the upper intersection 34 and the upper posterior strap retainer 58 at the upper intersection 32. The first and second straps connect to the upper frame assembly 12, 14 and their length and tension are adjustable in a substantially similar manner as described above with respect to the single upper posterior strap 52. It is likewise alternately within the scope of the present invention to substitute two lower posterior straps for the single lower posterior strap 54. In accordance with this alternative, a first lower posterior strap extends between the lower posterior strap retainer 60 at the lower intersection 44 and the lower posterior strap retainer 60 at the lower intersection 48. A second lower posterior strap extends between the lower posterior strap retainer 60 at the lower intersection 48 and the lower posterior strap retainer 60 at the lower intersection 46. The first and second straps connect to the lower frame assembly 16, 18 and their length and tension are adjustable in a substantially similar manner as described above with respect to the single lower posterior strap 54.

It is further understood that the specific means of connecting the securing straps 52, 54, 56 to the frame 10 is recited above by way of example and is not intended to limit the present invention. Although not shown, it is within the scope of the present invention to substitute alternate strap connection means known in the art for the instant strap retainers. For example, one or more strap retainers can be employed which are releasably, rather than permanently, attachable to the frame 10, such as in a snap-on manner, thereby enabling the user to disconnect and/or reconnect one or more of the securing straps 52, 54, 56 from the frame 10 without changing their length once the frame 10 has been fitted on a user and the desired lengths of the securing straps 52, 54, 56 have been set.

Although not shown, the frame 10 can additionally be provided with conventional lateral and medial knee condyle pads as well as upper and lower frame assembly padding to enhance the fit and stability of the frame on a leg of a user and to enhance the comfort of the user.

The frame 10 is described above as having two single-triangle truss units 12, 16 which are dynamically connected to one another by a pair of rotational hinges 20, 22, but do not share any common sides with one another. However, when the frame 10 is in a position of full extension, it resembles the structure of a three-triangle truss which can be characterized as a network of three intertwined truss units serially positioned within the truss, wherein each truss unit shares a common side with the adjacent truss unit. The three triangular units of the truss are in series the upper truss unit 12, a middle truss unit and the lower truss unit 16. The upper and lower truss units 12, 16 are as described above. The middle truss unit, like the upper and lower truss units, 12, 16, is made up of three interconnected triangular middle support elements, each of which constitutes a side of a triangle. The middle support elements are a middle first cross beam, a middle second cross beam, and a middle longitudinal strut. The middle longitudinal strut is preferably substantially vertical and comprises in combination the upper and lower longitudinal members 14, 18 which intersect at the first hinge 20. The middle first cross beam is a shared support element with the upper truss unit 12. This common support element is described above with respect to the upper second cross beam 28 and the same description applies equally to the middle first cross beam of the middle truss unit. As such, the middle first cross beam 28 is preferably diagonal relative to the middle longitudinal strut 14, 18. The middle second cross beam is a shared support element with the lower truss unit 16. This common support element is described above with respect to the lower second cross beam 42 and the same description applies equally to the middle second cross beam of the middle truss unit. As such, the middle second cross beam 42 is preferably diagonal relative to the middle longitudinal strut 14, 18.

In accordance with one embodiment shown in FIGS. 1-4, the middle truss unit substantially approximates an isoceles triangle with the middle first and second cross beams 28, 42 intersecting at the second hinge 22 approximating the substantially equal length sides of the triangle while the middle longitudinal strut 14, 18 has a substantially greater length. In accordance with alternate embodiments not shown, the middle truss unit substantially approximates a scalene triangle with all sides of the triangle being of unequal length.

The specific configuration and characteristics of the above-described frame 10 achieve a number of functional advantages when the frame 10 is mounted on the leg of a user. In particular, the trussed triangulate construction of the frame 10 provides it with a substantially greater degree of rigidity than conventional frames which correspondingly enhances the protective value and functional performance of the frame 10. The trussed triangulate construction and associated strapping system of the frame 10 also beneficially enhances the suspension of the frame 10 on a leg of a user relative to conventional frames. Suspension is the ability of the frame 10 to retain its proper placement on the leg during routine user activity. The properly mounted and strapped frame 10 resists undesirable translational (upward or downward) and/or rotational migration of the frame 10 on the leg to maintain optimal positioning of the frame on the leg relative to the knee during routine user activity. As such, enhanced suspension enhances the functional performance of the frame 10 and the comfort of the user.

While the forgoing preferred embodiments of the invention have been described and shown, it is understood that alternatives and modifications, such as those suggested and others, may be made thereto and fall within the scope of the invention.

I claim:

1. A frame for an orthopedic brace comprising:
an upper frame assembly;
a lower frame assembly;
a first hinge dynamically connecting a first side of said upper frame assembly and a first side of said lower frame assembly; and
a second hinge dynamically connecting a second side of said upper frame assembly and a second side of said lower frame assembly, wherein said upper or lower frame assembly includes a longitudinal member engaging said first hinge on said first side of said upper or lower frame assembly and a truss unit engaging said second hinge on said second side of said upper or lower frame assembly, said truss unit defining a triangle with a first side of said triangle being a substantially vertical longitudinal strut, a second side of said triangle being a first cross beam and a third side of said triangle being a diagonal second cross beam, said longitudinal strut engaging said second cross beam at a first intersection, said longitudinal strut engaging said first cross beam at a second intersection, and said longitudinal member, said first cross beam and said second cross beam engaging one another at a third intersection.

2. The frame of claim 1, wherein said first and second sides of said upper or lower frame assembly each has a truss fraction, wherein said truss fraction of said first side is the width of said first cross beam at said third intersection divided by the distance between said third intersection and said first hinge and said truss fraction of said second side is the distance between said first and second intersections divided by the distance between said second intersection and said second hinge, and wherein said truss fraction of said first side is substantially less than said truss fraction of said second side.

3. The frame of claim 2, wherein said truss fraction of said first side is less than about 30% and said truss fraction of said second side is greater than about 70%.

4. The frame of claim 2, wherein said truss fraction of said first side is less than about 40% and said truss fraction of said second side is greater than about 60%.

5. The frame of claim 1, wherein said first cross beam is substantially horizontal or diagonal.

6. The frame of claim 1, wherein said longitudinal member is an upper longitudinal member of said upper frame assembly, said truss unit is an upper truss unit of said upper frame assembly, said longitudinal strut is an upper longitudinal strut of said upper frame assembly, said first cross beam is an upper first cross beam of said upper frame assembly, said second cross beam is an upper second cross beam of said upper frame assembly, said first intersection is an upper first intersection of said upper frame assembly, said second intersection is an upper second intersection of said upper frame assembly and said third intersection is an upper third intersection of said upper frame assembly.

7. The frame of claim 1, wherein said longitudinal member is a lower longitudinal member of said lower frame assembly, said truss unit is a lower truss unit of said lower frame assembly, said longitudinal strut is a lower longitudinal strut of said lower frame assembly, said substantially first cross beam is a lower first cross beam of said lower frame assembly, said second cross beam is a lower second cross beam of said lower frame assembly, said first intersection is a lower first intersection of said lower frame assembly, said second intersection is a lower second intersection of said lower frame assembly and said third intersection is a lower third intersection of said lower frame assembly.

8. The frame of claim 1, further comprising securing strapping connected to said upper or lower frame assembly, said securing strapping posteriorly and diagonally extending relative to said longitudinal strut from said second intersection to said third intersection and extending from said third intersection to said first intersection, thereby defining a V-shaped strap pathway.

9. The frame of claim 8, wherein said securing strapping is a first securing strap and a second securing strap, and further wherein said first securing strap extends from said second intersection to said third intersection and said second securing strap extends from said third intersection to said first intersection.

10. The frame of claim 8, wherein said securing strapping is a single securing strap extending from said second intersection to said third intersection and from said third intersection to said first intersection.

11. A frame for an orthopedic brace comprising:
an upper frame assembly;
a lower frame assembly;
a first hinge dynamically connecting a first side of said upper frame assembly and a first side of said lower frame assembly; and
a second hinge dynamically connecting a second side of said upper frame assembly and a second side of said lower frame assembly, wherein said upper frame assembly includes an upper longitudinal member engaging said first hinge on said first side of said upper frame assembly and an upper truss unit engaging said second hinge on said second side of said upper frame assembly, said upper truss unit defining a triangle with a first side of said triangle being a substantially vertical upper longitudinal strut, a second side of said triangle being an upper first cross beam and a third side of said triangle being a diagonal upper second cross beam, said upper longitudinal strut engaging said upper second cross beam at an upper first intersection, said upper longitudinal strut engaging said upper first cross beam at an upper second intersection and said upper longitudinal member, said upper first cross beam and said upper second cross beam engaging one another at an upper third intersection and wherein said lower frame assembly includes a lower longitudinal member engaging said first hinge on said first side of said lower frame assembly and a lower truss unit engaging said second hinge on said second side of said lower frame assembly, said lower truss unit defining a triangle with a first side of said triangle being a substantially vertical lower longitudinal strut, a second side of said triangle being a lower first cross beam and a third side of said triangle being a diagonal lower second cross beam, said lower longitudinal strut engaging said lower second cross beam at a lower first intersection, said lower longitudinal strut engaging said lower first cross beam at a lower second intersection and said lower longitudinal member, said lower first cross beam and said lower second cross beam engaging one another at a lower third intersection.

12. The frame of claim 11, wherein said first and second sides of said lower frame assembly each has a lower truss fraction, wherein said lower truss fraction of said first side is the width of said lower first cross beam at said lower third intersection divided by the distance between said lower third intersection and said first hinge and said lower truss fraction of said second side is the distance between said lower first and second intersections divided by the distance between said lower second intersection and said second hinge, and wherein said lower truss fraction of said first side is substantially less than said lower truss fraction of said second side.

13. The frame of claim 11, further comprising a middle truss unit positioned between said upper and lower trusses, said middle truss unit approximating a triangle with a first side of said triangle being a substantially vertical middle longitudinal strut comprising said upper and lower longitudinal members intersecting at said first hinge, a second side of said triangle being a middle first cross beam comprising said upper second cross beam and a third side of said triangle being a middle second cross beam comprising said lower second cross beam, said second and third sides of said triangle intersecting at said second hinge.

14. The frame of claim 11, further comprising upper securing strapping connected to said upper frame assembly, said upper securing strapping posteriorly and diagonally extending relative to said upper longitudinal strut from said upper second intersection to said upper third intersection and extending from said upper third intersection to said upper first intersection, thereby defining a V-shaped upper strap pathway.

15. The frame of claim 11, further comprising lower securing strapping connected to said lower frame assembly, said lower securing strapping posteriorly and diagonally extending relative to said lower longitudinal strut from said lower second intersection to said lower third intersection and extending from said lower third intersection to said lower first intersection, thereby defining a V-shaped lower strap pathway.

16. The frame of claim 11, wherein said first and second sides of said upper frame assembly each has an upper truss fraction, wherein said upper truss fraction of said first side is the width of said upper first cross beam at said upper third intersection divided by the distance between said upper third intersection and said first hinge and said upper truss fraction of said second side is the distance between said upper first and second intersections divided by the distance between said upper second intersection and said second hinge, and wherein said upper truss fraction of said first side is substantially less than said upper truss fraction of said second side.

17. A frame for an orthopedic brace comprising:
an upper frame assembly;
a lower frame assembly;
a first hinge;
a second hinge, wherein said first hinge and said second hinge dynamically connect said upper and lower frame assemblies, and wherein said upper or lower frame assembly includes a longitudinal member engaging said first hinge on a first side of said upper or lower frame assembly and a truss unit engaging said second hinge on a second side of said upper or lower frame assembly, said truss unit defining a triangle with a first side of said triangle being a substantially vertical longitudinal strut, a second side of said triangle being a first cross beam and a third side of said triangle being a diagonal second cross beam, said longitudinal strut engaging said second cross beam at a first intersection, said longitudinal strut engaging said first cross beam at a second intersection, and said second cross beam engaging said first cross beam at a third intersection; and
a securing strapping connected to said upper or lower frame assembly, said securing strapping posteriorly and diagonally extending relative to said longitudinal strut from said second intersection to said third intersection and extending from said third intersection to said first intersection, thereby defining a V-shaped strap pathway.

18. A frame for an orthopedic brace comprising:
an upper frame assembly having an upper longitudinal member on a first side of said frame and an upper longitudinal strut on a second side of said frame;
a lower frame assembly;
a first hinge and a second hinge dynamically connecting said upper and lower frame assemblies;
an upper securing strap connected to a higher point on said upper longitudinal strut, posteriorly and diagonally extending relative to said upper longitudinal strut from said higher point on said upper longitudinal strut to a point on said upper longitudinal member, connected to said point on said upper longitudinal member, posteriorly and diagonally extending relative to said upper longitudinal strut from said point on said upper longitudinal member to a lower point on said upper longitudinal strut, and connected to said lower point on said upper longitudinal strut, thereby defining a V-shaped upper strap pathway for said upper securing strap from said higher point on said upper longitudinal strut to said point on said upper longitudinal member and back from said point on said upper longitudinal member to said lower point on said upper longitudinal strut.

19. The frame of claim 18, wherein said lower frame assembly has a lower longitudinal member on said first side of said frame and a lower longitudinal strut on said second side of said frame, said frame further comprising a lower securing strap connected to a lower point on said lower longitudinal strut, posteriorly and diagonally extending relative to said lower longitudinal strut from said lower point on said lower longitudinal strut to said lower longitudinal member, connected to said lower longitudinal member, posteriorly and diagonally extending relative to said lower longitudinal strut from said lower longitudinal member to an upper point on said lower longitudinal strut, and connected to said upper point on said lower longitudinal strut, thereby defining a V-shaped lower strap pathway for said lower securing strap from said lower point on said lower longitudinal strut to said lower longitudinal member and back to said upper point on said lower longitudinal strut.

20. A frame for an orthopedic brace comprising:
an upper frame assembly having a first upper support element on a first side of said frame and a second upper support element on a second side of said frame;
a lower frame assembly having a first lower support element on said first side of said frame and a second lower support element on said second side of said frame;
a first hinge on said first side of said frame dynamically connecting said upper frame assembly and said lower frame assembly by rotatably engaging said first upper support element and said first lower support element on said first side of said frame;
a second hinge on said second side of said frame dynamically connecting said upper frame assembly and said lower frame assembly by rotatably engaging said second upper support element and said second lower support element on said second side of said frame; and
an upper securing strap connected to a first point on said first upper support element, posteriorly and diagonally extending relative to said first upper support element from said first point to a point on said second upper support element, connected to said point on said second upper support element, posteriorly and diagonally extending from said point on said second upper support element to a second point on said first upper support element and connected to said second point on said first upper support element, thereby defining a V-shaped pathway for said upper securing strap from said first point on said first upper support element to said point on said second upper support element and back from said point on said second upper support element to said second point on said first upper support element.

21. The frame of claim 20, wherein said first and second upper support elements have a substantially vertical orientation when said frame is in a position of extension.

22. The frame of claim 20, wherein said first point is higher on said first upper support element than said second point when said frame is in a position of extension.

23. The frame of claim 20, wherein said lower frame assembly has a first lower support element on a first side of said frame and a second lower support element on a second side of said frame, said frame further comprising a lower securing strap connected to a first point on said first lower support element, posteriorly and diagonally extending relative to said first lower support element from said first point to a point on said second lower support element, connected to said point on said second lower support element, posteriorly and diagonally extending from said point on said second lower support to a second point on said first lower support element and connected to said second point on said lower support element, thereby defining a V-shaped pathway for said lower securing strap from said first point on said first lower support element to said point on said second lower support element and back to said second point on said first lower support element.

24. A frame for an orthopedic brace comprising:
an upper frame assembly having an upper longitudinal member on a first side of said frame and an upper longitudinal strut on a second side of said frame;
a lower frame assembly having a lower longitudinal member on said first side of said frame and a lower longitudinal strut on said second side of said frame;
a first hinge on said first side of said frame dynamically connecting said upper frame assembly and said lower frame assembly by rotatably engaging said upper longitudinal member and said lower longitudinal member on said first side of said frame;
a second hinge on said second side of said frame dynamically connecting said upper frame assembly and said lower frame assembly by rotatably engaging said upper longitudinal strut and said lower longitudinal strut on said second side of said frame;
an upper first securing strap and an upper second securing strap, wherein said upper first securing strap is connected to an upper point on said upper longitudinal strut, posteriorly and diagonally extends relative to said upper longitudinal strut from said upper point on said upper longitudinal strut to a point on said upper longitudinal member and is connected to said point on said upper longitudinal member, and wherein said upper second securing strap is connected to said point on said upper longitudinal member, posteriorly and diagonally extends relative to said upper longitudinal strut from said point on said upper longitudinal member to a lower point on said upper longitudinal strut, and is connected to said lower point on said upper longitudinal strut, thereby defining a V-shaped upper strap pathway for said upper first securing strap and said upper second securing strap in combination from said upper point on said upper longitudinal strut to said point on said upper longitudinal member and back from said point on said upper longitudinal member to said lower point on said upper longitudinal strut.

25. The frame of claim 24, wherein said lower frame assembly has a lower longitudinal member on said first side of said frame and a lower longitudinal strut on said second side of said frame, said frame further comprising a lower first securing strap and a lower second securing strap, wherein said lower first securing strap is connected to a lower point on said lower longitudinal strut, posteriorly and diagonally extends relative to said lower longitudinal strut from said lower point on said lower longitudinal strut to a point on said lower longitudinal member and is connected to said point on said lower longitudinal member, and wherein said lower second securing strap is connected to said point on said lower longitudinal member, posteriorly and diagonally extends relative to said lower longitudinal strut from said point on said lower longitudinal member to an upper point on said lower longitudinal strut, and is connected to said upper point on said lower longitudinal strut, thereby defining a V-shaped lower strap pathway for said lower first securing strap and said lower second securing strap in combination from said lower point on said lower longitudinal strut to said point on said lower longitudinal member and back from said point on said lower longitudinal member to said upper point on said lower longitudinal strut.

26. A frame for an orthopedic brace comprising:
an upper frame assembly having a first upper support element on a first side of said frame and a second upper support element on a second side of said frame;
a lower frame assembly having a first lower support element on said first side of said frame and a second lower support element on a second side of said frame;
a first hinge on said first side of said frame dynamically connecting said upper frame assembly and said lower frame assembly by rotatably engaging said first upper support element and said first lower support element on said first side of said frame;
a second hinge on said second side of said frame dynamically connecting said upper frame assembly and said lower frame assembly by rotatably engaging said second upper support element and said second lower support element on said second side of said frame; and
an upper first securing strap and an upper second securing strap, wherein said upper first securing strap is connected to a first point on said first upper support element, posteriorly and diagonally extends relative to said first upper support element from said first point to a point on said second upper support element and is connected to said point on said second upper support element, and wherein said upper second securing strap is connected to said point on said second upper support element, posteriorly and diagonally extends from said point on said upper second support to a second point on said first upper support element, and is connected to said second point on said first upper support element, thereby defining a V-shaped pathway for said upper first securing strap and said upper second securing strap in combination from said first point on said first upper support element to said point on said second upper support element and back from said point on said second upper support element to said second point on said first upper support element.

27. A frame for an orthopedic brace comprising:
a lower frame assembly having a first lower support element on a first side of said frame and a second lower support element on a second side of said frame;
an upper frame assembly having a first upper support element on said first side of said frame and a second upper support element on said second side of said frame;
a first hinge on said first side of said frame dynamically connecting said upper frame assembly and said lower frame assembly by rotatably engaging said first upper support element and said first lower support element on said first side of said frame;
a second hinge on said second side of said frame dynamically connecting said upper frame assembly and said lower frame assembly by rotatably engaging said second upper support element and said second lower support element on said second side of said frame; and
a lower securing strap connected to a first point on said first lower support element, posteriorly and diagonally extending relative to said first lower support element from said first point to a point on said second lower support element, connected to said point on said second lower support element, posteriorly and diagonally extending from said point on said second lower support element to a second point on said first lower support element and connected to said second point on said first lower support element, thereby defining a V-shaped pathway for said lower securing strap from said first point on said first lower support element to said point on said second lower support element and back from said point on said second lower support element to said second point on said first lower support element.

28. The frame of claim 27, wherein said first point is lower on said first lower support element than said second point when said frame is in a position of extension.

29. The frame of claim 27, wherein said first and second lower support elements have a substantially vertical orientation when said frame is in a position of extension.

30. The frame of claim 27, wherein said first lower support element is a lower longitudinal strut.

31. The frame of claim 27, wherein said second lower support element is a lower longitudinal member.

32. A frame for an orthopedic brace comprising:
an upper frame assembly having an upper longitudinal member on a first side of said frame and an upper longitudinal strut on a second side of said frame;
a lower frame assembly having a lower longitudinal member on said first side of said frame and a lower longitudinal strut on said second side of said frame;
a first hinge on said first side of said frame dynamically connecting said upper frame assembly and said lower frame assembly by rotatably engaging said upper longitudinal member and said lower longitudinal member on said first side of said frame;
a second hinge on said second side of said frame dynamically connecting said upper frame assembly and said lower frame assembly by rotatably engaging said upper longitudinal strut and said lower longitudinal strut on said second side of said frame;
a lower securing strap connected to a lower point on said lower longitudinal strut, posteriorly and diagonally extending relative to said lower longitudinal strut from said lower point on said lower longitudinal strut to a point on said lower longitudinal member, connected to said point on said lower longitudinal member, posteriorly and diagonally extending relative to said lower longitudinal strut from said point on said lower longitudinal member to an upper point on said lower longitudinal strut, and connected to said upper point on said lower longitudinal strut, thereby defining a V-shaped lower strap pathway for said lower securing strap from said lower point on said lower longitudinal strut to said point on said lower longitudinal member and back from said point on said lower longitudinal member to said upper point on said lower longitudinal strut.

33. A frame for an orthopedic brace comprising:
an upper frame assembly having an upper longitudinal member on a first side of said frame and an upper longitudinal strut on a second side of said frame;
a lower frame assembly having a lower longitudinal member on said first side of said frame and a lower longitudinal strut on said second side of said frame;
a first hinge on said first side of said frame dynamically connecting said upper frame assembly and said lower frame assembly by rotatably engaging said upper longitudinal member and said lower longitudinal member on said first side of said frame;
a second hinge on said second side of said frame dynamically connecting said upper frame assembly and said lower frame assembly by rotatably engaging said upper longitudinal strut and said lower longitudinal strut on said second side of said frame;
a lower first securing strap and a lower second securing strap, wherein said lower first securing strap is connected to a lower point on said lower longitudinal strut, posteriorly and diagonally extends relative to said lower longitudinal strut from said lower point on said lower longitudinal strut to a point on said lower longitudinal member and is connected to said point on said lower longitudinal member, and wherein said lower second securing strap is connected to said point on said lower longitudinal member, posteriorly and diagonally extends relative to said lower longitudinal strut from said point on said lower longitudinal member to an upper point on said lower longitudinal strut, and is connected to said upper point on said lower longitudinal strut, thereby defining a V-shaped lower strap pathway for said lower first securing strap and said lower second securing strap in combination from said lower point on said lower longitudinal strut to said point on said lower longitudinal member and back from said point on said lower longitudinal member to said upper point on said lower longitudinal strut.

34. A frame for an orthopedic brace comprising:
an upper frame assembly having a first upper support element on a first side of said frame and a second upper support element on a second side of said frame;
a lower frame assembly having a first lower support element on said first side of said frame and a second lower support element on a second side of said frame;
a first hinge on said first side of said frame dynamically connecting said upper frame assembly and said lower frame assembly by rotatably engaging said first upper support element and said first lower support element on said first side of said frame;
a second hinge on said second side of said frame dynamically connecting said upper frame assembly and said lower frame assembly by rotatably engaging said second upper support element and said second lower support element on said second side of said frame; and
a lower first securing strap and a lower second securing strap, wherein said lower first securing strap is connected to a first point on said first lower support element, posteriorly and diagonally extends relative to said first lower support element from said first point to a point on said second lower support element and is connected to said point on said second lower support element, and wherein said lower second securing strap is connected to said point on said second lower support element, posteriorly and diagonally extends from said point on said second lower support element to a second point on said first lower support element, and is connected to said second point on said first lower support element, thereby defining a V-shaped pathway for said lower first securing strap and said lower second securing strap in combination from said first point on said first lower support element to said point on said second lower support element and back from said point on said second lower support element to said second point on said first lower support element.

35. The frame of claim 34, wherein said upper frame assembly has a first upper support element on a first side of said frame and a second upper support element on a second side of said frame, said frame further comprising an upper first securing strap and an upper second securing strap, wherein said upper first securing strap is connected to a first point on said first upper support element, posteriorly and diagonally extends relative to said first upper support element from said first point to a point on said second upper support element and is connected to said point on said second upper support element, and wherein said upper second securing strap is connected to said point on said second upper support element, posteriorly and diagonally extends from said point on said upper second support to a second point on said first upper support element, and is connected to said second point on said first upper support element, thereby defining a V-shaped pathway for said upper first securing strap and said upper second securing strap in combination from said first point on said first upper support element to said point on said second upper support element and back to said second point on said first upper support element.

* * * * *